United States Patent [19]

Valdès Sosa et al.

[11] Patent Number: 5,282,474
[45] Date of Patent: Feb. 1, 1994

[54] METHOD AND SYSTEM FOR THE EVALUATION AND VISUAL DISPLAY OF ABNORMAL ELECTROMAGNETIC PHYSIOLOGICAL ACTIVITY OF THE BRAIN AND THE HEART

[75] Inventors: Pedro A. Valdès Sosa, La Lisa; Rolando B. Lirio, Havana; Roberto D. Pascual Marqui, Havana; Livia N. Blaquier, Havana; Lidice G. Garcia, Havana; Juan C. Jiménez Sobrino, Havana; Jorge B. Bayard, Havana, all of Cuba

[73] Assignee: Centro de Neurociencias de Cuba, Cuba

[21] Appl. No.: 790,383

[22] Filed: Nov. 8, 1991

[30] Foreign Application Priority Data

Nov. 9, 1990 [CU] Cuba ............................ 169/90

[51] Int. Cl.⁵ .......................................... A61B 5/0205
[52] U.S. Cl. ................................ 128/670; 128/696; 128/731
[58] Field of Search .................. 128/670, 696, 731

[56] References Cited

U.S. PATENT DOCUMENTS

| | | | |
|---|---|---|---|
| 4,417,592 | 11/1983 | John | 128/731 |
| 4,421,121 | 12/1983 | Whisler et al. | 128/731 |
| 4,421,122 | 12/1983 | Duffy | 128/731 |
| 4,649,482 | 3/1987 | Raviv et al. | 128/731 X |
| 4,846,190 | 7/1989 | John | 128/731 |
| 4,913,160 | 4/1990 | John | 128/731 |
| 4,974,598 | 12/1990 | John | 128/696 |
| 4,974,602 | 12/1990 | Abraham-Fuchs et al. | 128/731 |
| 5,046,504 | 9/1991 | Albert et al. | 128/696 |

FOREIGN PATENT DOCUMENTS

| | | |
|---|---|---|
| 0485300 | 5/1992 | European Pat. Off. |
| 3331458 | 4/1984 | Fed. Rep. of Germany |
| WO82/03977 | 11/1982 | World Int. Prop. O. |

OTHER PUBLICATIONS

Gevins, A. S. and Remond, A., *Handbook of Electroencephalography and Clinical Neurophysiology*, 1987, pp. 1-30, 318-539, Amsterdam.
Gonzalez-Andino, S., *Brain Electrical Field Measurements Unaffected by Linked Earlobes Reference*, 1990, pp. 155-160, vol. 75, Ireland.
Nunez, P. L. *Electrical Fields of the Brain*, 1981, pp. 177-213, New York.
Valdes et al., "QEEG in a Public Health System," *Brain Topography*, 1991.
Biscay, R. et al., *Localization Error in Biomedical Imaging*, 1992, Cuba, pp. 1-19.
Szava, S. et al., *High Resolution Quantitative EEG Analysis*, 1993, Cuba.
Prenter, P. M., *Splines and Variational Methods*, 1975, New York, pp. 135-137.
Mardia, K. V. et al., *Multivariate Analysis*, 1979, London.
Brillinger, D. R., *Time Series Data Analysis and Theory*, 1975, New York, pp. 88-115.
Valdes, P. et al., *Brain Topography* 3, No. 1, 1990, pp. 281-282.
Cox, D. P. et al., *Theoretical Statistics*, London, pp. 286-333.
Taikang Ning et al., "Bispectral Analysis of the EEG During Various Vigilance States," Proceedings of the 9th Annual Conference of the IEEE Engineering in Medicine and Biology Society; IEEE Press; New York, U.S. vol. 2/4, Nov. 13, 1987, pp. 943-944.
Valdes et al., "High Resolution Spectral EEG Norms for Topography," vol. 3, No. 1, 1990, pp. 281-282.

Primary Examiner—William E. Kamm
Assistant Examiner—Jeffrey R. Jastrzab
Attorney, Agent, or Firm—Bacon & Thomas

[57] ABSTRACT

A method and system for the evaluation and visual display of abnormal electromagnetic physiological activity of the brain and the heart utilizes a set of bioelectric amplifiers and a computer based system for the recording and analog to digital conversion of human electrophysiological signals. The signals collected are expanded in selected spatio-temporal functional bases, and parametric models are used for summarizing the statistical properties of the coefficients. Multivariate topographic maps and curves are computed based on the comparison of the estimated parameters for a patient and the regression equations for the parameters calculated from a normative database. The multivariate maps and curves are visually displayed in a diagnostically useful color-coded probability scale.

9 Claims, 6 Drawing Sheets

METHOD AND SYSTEM FOR THE EVALUATION AND VISUAL DISPLAY OF ABNORMAL ELECTROMAGNETIC PHYSIOLOGICAL ACTIVITY OF THE BRAIN AND THE HEART

BACKGROUND OF THE INVENTION

1. Field of the Invention

The present invention relates to electronic computerized medical instruments and more particularly to the analysis and display of bioelectromagnetic signals of the brain and the heart for detecting abnormal functioning by a non-invasive computerized system and method.

2. Description of Related Art

Classical electroencephalography (EEG) and electroencephalography (EKG) are techniques for the diagnosis of of brain and heart dysfunctions that have been demonstrated to be useful for a number of decades. These methods are largely based on the skill, memory, and experience of a neurologist or cardiologist that examines tracings of bioelectric activity recorded upon paper. Recently, biomagnetic measurements of both the heart and brain have been introduced for the same purposes. Thus, a patient may be examined with any of the following techniques that yield information about current source generators in the human body: electroencephalography (EEG), magnetoencephalography (MEG), brain evoked response (ER), electrocardiography (EKG), and magnetocardiography (MKG).

In recent years computerized techniques for recording, analyzing and visually displaying electromagnetic signals of the brain and the heart have been introduced, in an attempt to achieve greater objectivity in diagnostic procedures as well as uncovering subtle dysfunctions otherwise difficult to detect except by a highly trained specialist.

The current state of the art, as reflected in U.S. Pat. Nos. 4,417,592; 4,421,122; 4,913,160; and 4,974,598 is as follows:

a) Selected features of the electromagnetic signals of a patient are extracted by means of different data transforms, amongst which the most prominent are: no transform (working with the raw data), broad band spectral analysis, and the Karhunen Loeve expansions.

b) These features are subjected to statistical comparison with standards extracted from a database of normal subjects.

c) As a final result, topographic maps are displayed of the head and torso (for brain and heart data respectively) in which the intensity of deviation from the norm are color-coded in terms of univariate statistical distributions.

There is abundant evidence (Valdes et al., QEEG in a public health system, Invited lecture at the 2d Congress of Brain Electromagnetic Topography, Brain Topography, 1991, in press) that these procedures are clinically useful in both specialized medical care as well in public health facilities. In spite of these promising results the sensitivity and specificity of these procedures has been limited to date by a number of factors that include:

i) The feature sets defined to date are too large, presenting multiple multivariate statistical colinearities. Thus, problems arise as to the definition of probability scales and the decision as to whether a deviation in a probability map is actually abnormal. Duffy et al. (Quantified Neurophysiology with Mapping: Statistical Inference, Exploratory and Confirmatory; Data Analysis, Brain Topography Vol. 3 No. 1, Fall 1990 pp. 3-12) have demonstrated the excessively high false positive rates created by this situation.

ii) The data transforms used to date, while useful in some situations, have been demonstrated (Valdes et al.,High Resolution Spectral EEG Norms for Topography, Brain Topography Vol. 3 No. 1, Fall 1990 pp. 281-282) to be too coarse to reconstruct the profile of many abnormalities.

iii) Topographic maps and curves of features are constructed without taking into consideration the high correlation of features due to biological constraints being in fact univariate projections of patient data in which the abnormalities may be multivariate.

iv) Topographic maps and curves representing a vector of features are currently color-coded only using the marginal (univariate) probability distribution of each component of the vector. This increases the probability of false positive findings when searching for significant regions in the whole map or curve.

SUMMARY OF THE INVENTION

It is accordingly an objective of the present invention to provide a method and system for the evaluation and visual display of abnormal electromagnetic physiological activity of the brain and heart for the calculation of topographic maps with increased sensitivity and specificity.

In accordance with a first preferred embodiment of the present invention there is provided a method for evaluating and displaying the abnormal electromagnetic physiological activity of a patient. The preferred method includes the steps of:

a) Attaching or approximating a set of electrodes and magnetic sensors to the scalp or torso of a patient to detect electromagnetic physiological activity in the form of an electroencephalogram (EEG), a magnetoencephalogram (MEG), a brain evoked response (ER), an electrocardiogram (EKG), and/or a magnetocardiogram (MKG);

b) Amplifying the electromagnetic signals detected at each electrode and magnetic sensor;

c) Obtaining on-line digital spatio-temporal signals, consisting of the EEG, MEG, ER, EKG, and/or MKG, by connecting analog-digital converters to each amplifier, and digitizing all data as it is gathered;

d) Obtaining sets of the spatio-temporal signals for the patient, and computing the coefficients of its expansions in a spatio-temporal functional basis defined by the tensorial product of selected functional bases for the spatial and temporal domains;

e) Computing estimates of the parameters determined by statistical parametric models for the probabilistic moments of the coefficients for a patient;

f) Automatically constructing of summarized topographic maps by a process of diagnostically useful summarization of the information contained in the sets of signals or probabilistic moments corresponding to different instants or frequencies, and automatically constructing of summarized curves by a process of summarization of the information contained in the sets of signals or probabilistic moments corresponding to different electrodes and magnetic sensors;

g) Computing multivariate topographic maps and curves based on the comparison of the summarized topographic maps and curves with their means, standard deviations and correlations in stored normative data bases from normal subjects;

h) Visually displaying the multivariate topographic maps and curves in a diagnostically useful color-coded probability scale.

In accordance with a second preferred embodiment of the invention there is provided a system for evaluating and displaying the abnormal electromagnetic physiological activity of a patient. The system includes:

a) A set of electrodes and/or magnetic sensors adapted to be attached or approximated to the scalp or torso of a patient in order to detect electromagnetic physiological activity in the form of an electroencephalogram (EEG), a magnetoencephalogram (MEG), a brain evoked response (ER), an electrocardiogram (EKG), and/or a magnetocardiogram (MKG);

b) A system for the amplification of the aforementioned physiological activity;

c) Means for the analog-to-digital conversion of the preamplified physiological activity in the form of digital spatio-temporal signals, representative of the aforementioned EEG, MEG, ER, EKG, and/or MKG;

d) Means for storing sets of said spatio-temporal signals for the patient, and for computing the coefficients of its expansions in a spatio-temporal functional basis defined by the tensorial product of selected functional bases for the spatial and temporal domains;

e) Means for computing estimates of the parameters determined by statistical parametric models for the moments of the coefficients for a patient;

f) Means for the automatic construction of summarized topographic maps by a process of diagnostically useful summarization of the information contained in the sets of signals or probabilistic moments corresponding to different instants or frequencies, and automatic construction of summarized curves by a process of summarization of the information contained in the sets of signals or probabilistic moments corresponding to different electrodes and magnetic sensors;

g) Means for computing multivariate topographic maps and curves for a given patient based on the comparison of the summarized topographic maps and curves with their means, standard deviations and correlations in stored normative data bases from normal subjects;

h) Means for visually displaying the multivariate topographic maps and curves in a diagnostically useful color-coded probability scale.

BRIEF DESCRIPTION OF THE DRAWINGS

In order that the invention may be better understood, further detailed description follows with reference to the accompanying drawings in which.

DETAILED DESCRIPTION OF THE PREFERRED EMBODIMENTS

Figure 1:
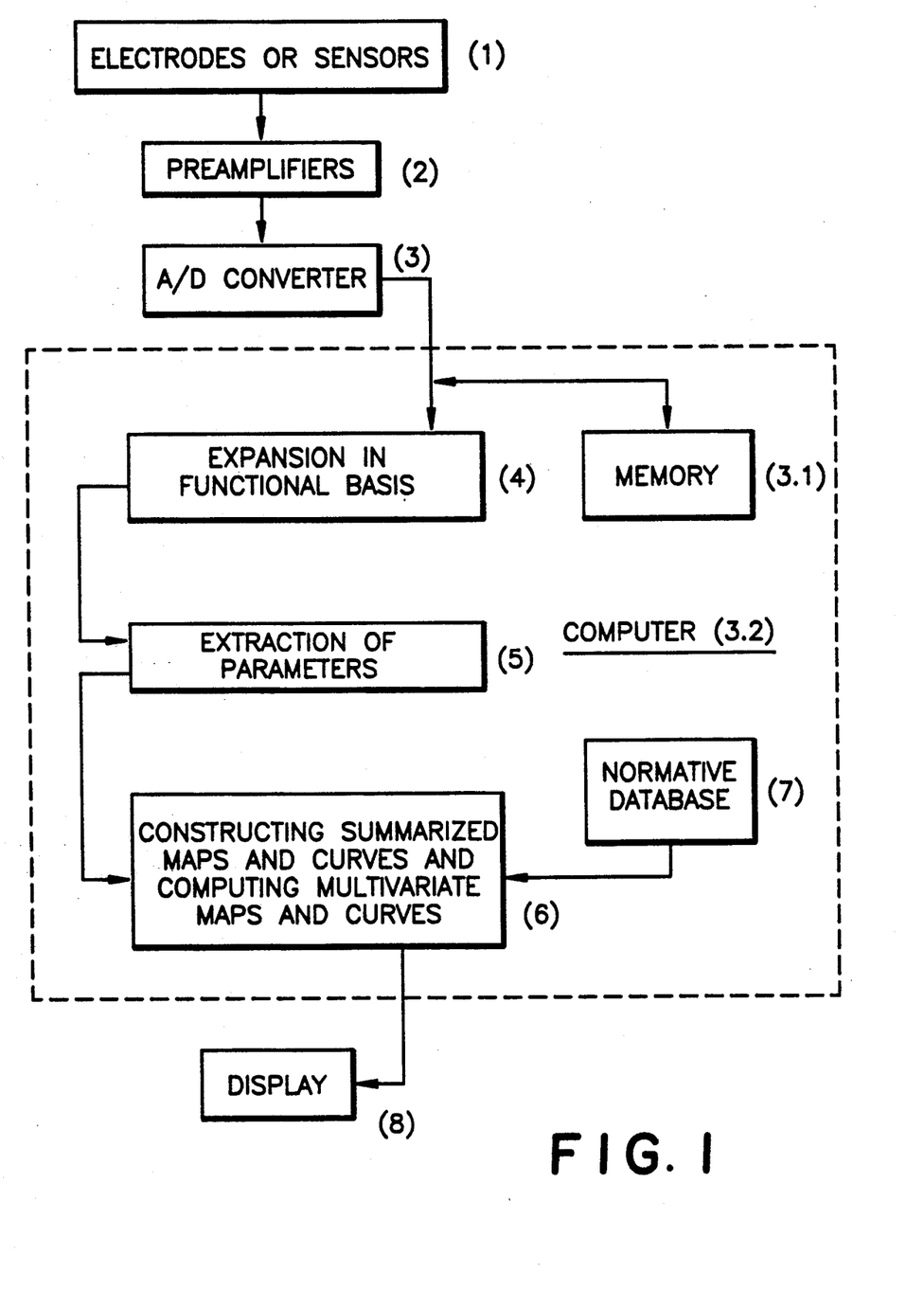
FIG. 1 is a block schematic drawing of one embodiment of the present invention.

The detection of the patient's physiological activity may be made using a plurality of conventional detectors (electrodes) for electrical activity and magnetometers or gradiometers for the magnetic activity. The sensors and detectors (1) will be placed according to a predefined plan in order to maximize the amount of information to be extracted from the bioelectromagnetic signals, in particular the sensor (detector) array will be placed in proximity or upon the head (torso) for the study of brain (heart) activity.

The electric and/or magnetic (termed henceforth electromagnetic) signals are amplified (2) to the dynamic range of an Analog to Digital converter (3), which converts the signals into numbers that are stored in the memory (3.1) of a general purpose digital computer (3.2).

Let $Y(x_m, t_n)$ denote the electromagnetic signal recorded at time $t_n$ ($t_1, \ldots, t_n$ are the times of digitization). Information is recorded in buffers of size n called segments and which are the complete set of samples for M sensor/detectors and a time period of size $T=n\Delta t$, where $\Delta t$ is the sampling period.

Segments are projected upon the tensor product of a spatial basis $\{A_1(x), A_2(x), \ldots\}$ and a temporal basis, $\{B_1(t), B_2(t), \ldots\}$, by least squares fitting of the expansion:

$$Y(x,t) = \Sigma\Sigma C_{ij} A_i(x) B_j(t) \qquad (1)$$

in terms of which the data $Y(x_m, t_n)$ is now represented by the coefficients $C_{ij}$ (4). This representation has advantages in terms of data compression, statistical orthogonalization and interpretation, though the specific basis, and the number of its elements, must be selected according to the type of data collected by the user.

Important temporal bases to be used are:

a) The canonical vector basis in $\mathbb{R}^N$, which reduces to using the raw data for analyzing instantanous temporal phenomena.

b) The Fourier basis $B_j(t) = \exp(iw_j t)$ which transforms the data into the frequency domain for the analysis of stationary stochastic phenomena.

c) The Karhunen-Loeve basis, eigenfunctions of the second order moments of the signal, either in the time or frequency domain, also known as Principal Components for the analysis of general stochastic phenomena.

d) The wavelet basis on the real line, of the form: $B_j(t) = g((t-a_{j1})/b_{j2})$ or $B_j(t) = g(t-a_{j1})\exp(iw_{j2})$ where g is a convenient waveform or mother wavelet(e.g. a Gaussian), $j=(j_1,j_2)$, and $a_{j1}$ is interpreted as a translation parameter, $b_{j2}$ as a scale parameter and $w_{j2}$ as a modulation (frequency) parameter. This type of basis is convenient for time localization of nonstationary stochastic phenomena and multiresolution analysis.

Important spatial bases to be used are:

a) The canonical vector basis in $\mathbb{R}^M$, which reduces to using the raw data for analyzing instantanous spatial phenomena.

b) The Karhunen-Loeve basis, eigenfunctions of the second order moments of the signal, in the space domain.

c) Spatial spline basis of the general form:

$$B_j(x) = \Sigma \psi_k(x) \psi_k^*(x_j) / \lambda_k$$

where $\psi_k$ and $\lambda_k$ are, respectively, the eigenfunctions and eigenvalue of an operator D that acts upon functions defined over the surface S on which the sensors/detectors are placed or approximated, $x_j$ being their position. This basis has the property that it may be used to represent any function f on S that interpolates the points $x_j$ with arbitrary values $y_j$ under the restriction of being the smoothest in the sense of minimizing $\|Df\|$, in particular for S spheres S, (approximation to the head or torso)

$$B_j(x) = \Sigma\Sigma Y_{lm}(x) Y_{lm}^*(x_j) / [l(l+1)]^2$$

where $Y_{lm}$ are the spherical harmonic functions.

The statistical properties of the coefficients of the spatio temporal signals are summarized by their statistical moments. For reasons of simplicity only up to second order moments will be considered (all the information necessary for Gaussian processes):

$$\mu_{ij} = E(C_{ij})$$

$$\mu_{ijkl} = E(C_{ij} C_{kl}^*)$$

where $E()$ is the expectation operator and * is a transpose conjugation operator.

These moments are described in terms of a minimal set of parameters $\theta$:

$$\mu_{ij} = \mu_{ij}(\theta)$$

$$\mu_{ijkl} = \mu_{ijkl}(\theta)$$

where $\theta$ is a vector of parameters and the $\mu(.)$ are known functions. This parametric description reduces the size of final parameter set based upon the smoothness of variation of the statistical moments in the spatial and temporal domains.

Important parametric models to be used for the statistical moments of the coefficients are:

1) The model defined by taking the moments as parameters, so that no functional structure is introduced. A remarkable example is the case where the vector of parameters is the discrete spectrum at each electrode or sensor (i.e. the second order moments of the coefficients associated with the Fourier expansion for the time domain).

2) The model obtained by considering the vector of coefficients $C(t) = (C_j(t))$ of a spatial expansion $$Y(x,t) = \Sigma\Sigma C_{ij} A_i(x) B_j(t) = \Sigma C(t) A_j(x)$$

as a multivariate autoregressive time series. Thus, the second order statistical moments are functions of the autoregressive parameters.

3) Sources models, such as a multiple dipole source model, with or without varying locations and moments. In this type of model the statistical moments of the coefficients are parameterized by taking the statistical moments of the source as parameters.

In general the specific parametric model must be selected according to the type of data collected by the user.

The extraction of parameters (5) for a given patient consists of computing its estimate $\bar{\theta}$ by minimizing a statistical distance (least squares or maximum likelihood metric) between the parameterized statistical moments m and the sample moments (averaging across all the time segments recorded).

The trends and variabilities of the estimated parameters V (may be transformed in order to achieve a Gaussian distribution, $V = T(\theta)$) are analyzed by means of regression equations:

$$V = g(u; \beta) + e$$

where e is a random vector with zero mean and vector of variances $h(u;\gamma)$; $g(u;\beta)$ is the mean regression function; and $\beta$ and $\gamma$ are the vectors of unknown coefficients in the expansions of g and h in given functional bases respectively. The functions g and h allows accounting for the smoothness of the variation of V as function of the age and other covariables included in u.

These regression equations are fitted (using least squares regression analysis) to the data corresponding to a large sample of normal subjects. A Normative Database (7) stores all the information about the trends and variabilities associated with the aforementioned regression equations in the normal population, which include: i) the estimations of the mean regression function g (i.e. the estimate $\hat{B}$ of $\beta$), and also the variances and correlations of: ii) the vector of residuals of the parameters, $V-g(u;\hat{\beta})$, iii) the vector of residuals of the moments of the coefficients, $m - \mu(\hat{\theta})$, where $\hat{\theta}$ is the maximum likelihood estimator for $\theta$, calculated using statistical formulas well-known to those skilled in the art and iv) the vector of residuals of the original signals, $Y(x,t) - \hat{Y}(t,x)$. Here $\#Y(x,t)$ denotes the predicted value of Y:

$$\hat{Y}(x,t) = \Sigma\Sigma \hat{C}_{ij} A_i(x) B_j(t)$$

where $\hat{C}_{ij}$ is the predicted value of $C_{ij}$ using the estimated first order moment $\mu_j(\hat{\theta})$.

Given a patient's data, the information stored in the normative database (7) is used to compute multivariate topographic maps M(x) and curves Q(v) (6), the symbols M(x) and Q(v) denoting a patient's multivariate map and curve respectively. M(x) is any spatial vector of features, Q(v) is a temporal or frequency vector of features.

In what follows, Z generically denotes a map or a curve and $\mu$ and $\Sigma$ shall refer to its mean vector and dispersion matrix in the normal population. From Z the following multivariate maps and curves are calculated:

a) Typified conditional residual Maps or curves defined by $R = (Z - \hat{Z})$, where $\hat{Z}$ is the vector with components $\hat{Z}_j = E(Z_j - Z^{(j)})$, the conditional expected value of $Z_j$ given the rest of the components of Z. This vector is scaled in terms of its standard deviation.

b) Typified Maximal Abnormality Directional Map or Curve defined by $R = \Sigma^{-1} Z$ which is the direction which maximizes $(R'Z)^2 / (R'\Sigma R)$. This vector is also scaled in terms of its standard deviation.

The multivariate Map or Curve is visually displayed as a color coded map in which the intensity value $I_j$ of a given pixel is scaled according to:

$$Ij = \begin{cases} 1 - F(Rj), & \text{when high values of } Rj \text{ are abnormal} \\ G(Rj), & \text{when low values of } Rj \text{ are abnormal} \end{cases}$$

where F() and G() are, respectively, the probability distribution function of the maximum and the minimum of the vector R in the normal population.

Figure 2:
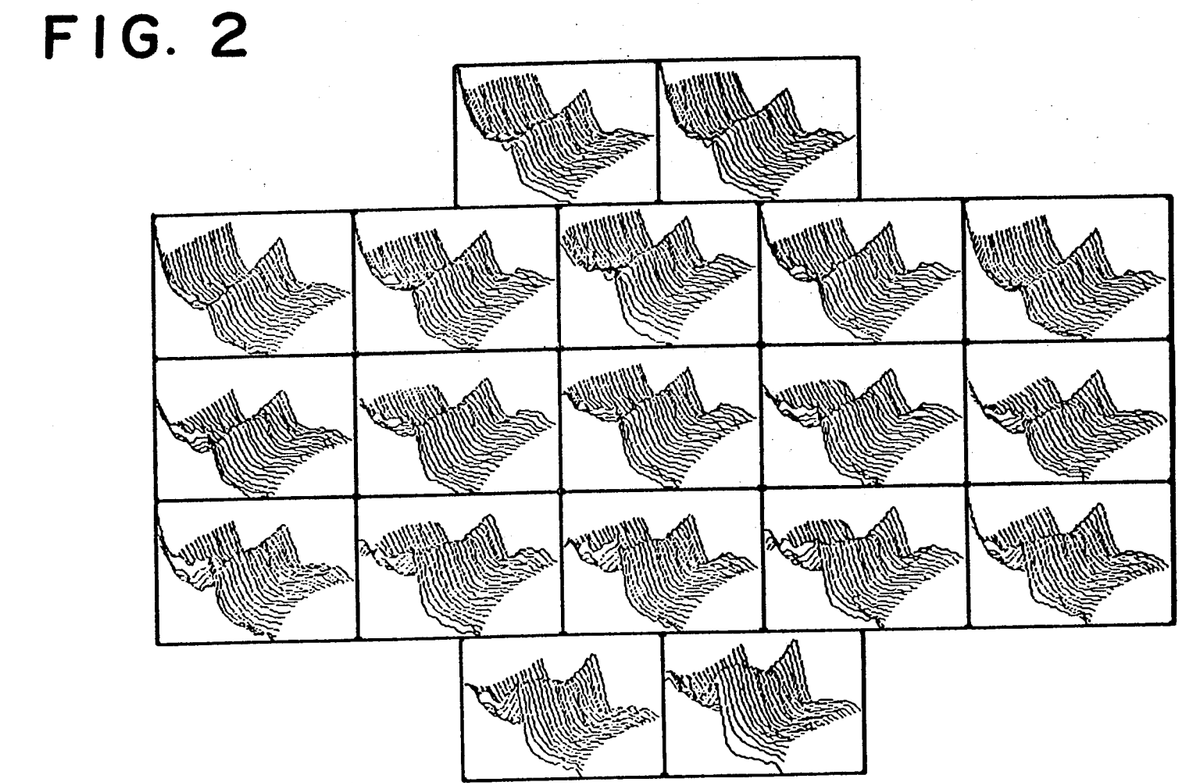
FIG. 2 shows the regression surfaces determined by the development of the EEG spectrum at each electrode as a function of the age of the subject in the normal population.

Examples of the use of these procedures in clinical material will now be given. If one uses as the spatial basis the canonical one, as a temporal basis the Fourier basis, a high resolution frequency decomposition of the EEG may be obtained. The parameters of interest are the variances of the Fourier coefficients (spectra) at each derivation. The age dependent regression equations for the normal population are expressed as tensor products of a frequency spline basis and polynomial functions for age dependency. FIG. 2 illustrates the frequency-age mean value for the log spectra in all derivations of the 10/20 system. The multivariate map for a given frequency and curve for a given derivation are termed in this case the high resolution "z ma" and "z spectrum", respectively.

Figure 3:
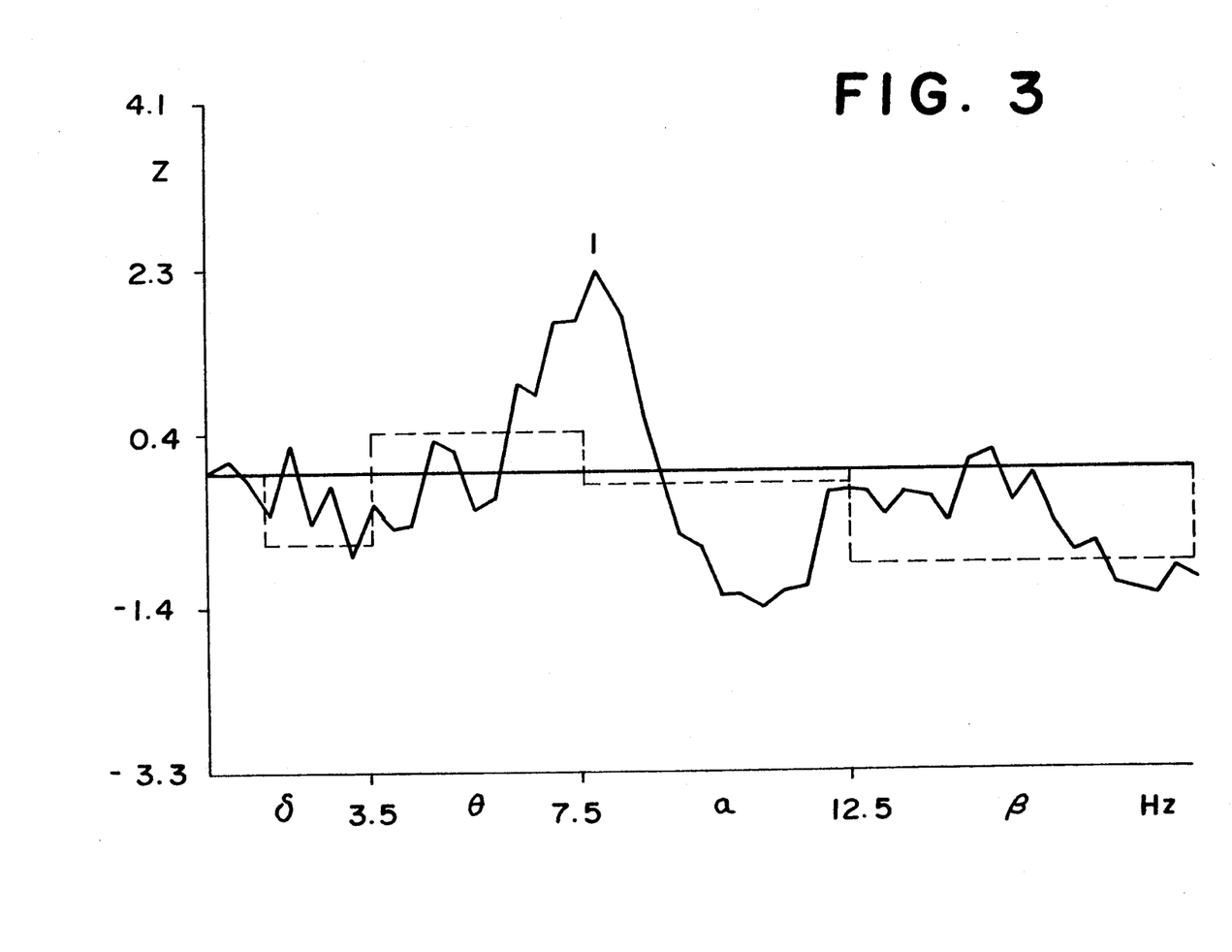
FIG. 3 shows the narrow band Z-spectrum at derivation P4 of a patient with a right parietal meningioma as compared to the Broad Band Spectral representation of the same patient.

FIG. 3 illustrates the higher sensitivity of the high resolution Z-spectrum at derivation P4 of a patient with a right parietal meningioma (dark curve) as compared to traditional Broad Band Spectral representation (light curve) of the same patient.

Figure 4:
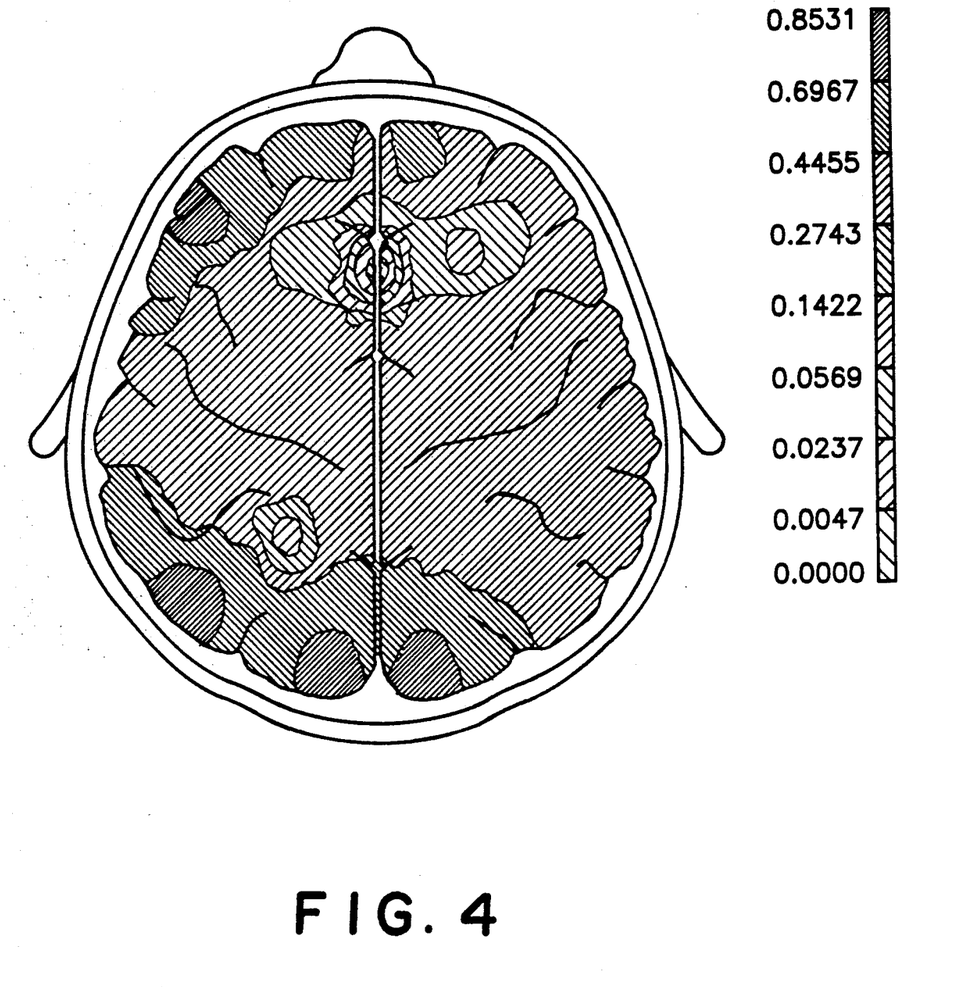
FIG. 4 shows the Z map corresponding to the maximal deviation with a maximum probability scale for a patient with a central cyst detected by Nuclear magnetic resonance.

At the frequency of maximum abnormality evidenced in FIG. 3, a multivariate Z map (FIG. 4) coded with a maximum probability scale shows the most extreme values at the same location that a central cyst was detected by Nuclear magnetic resonance.

Figure 5:
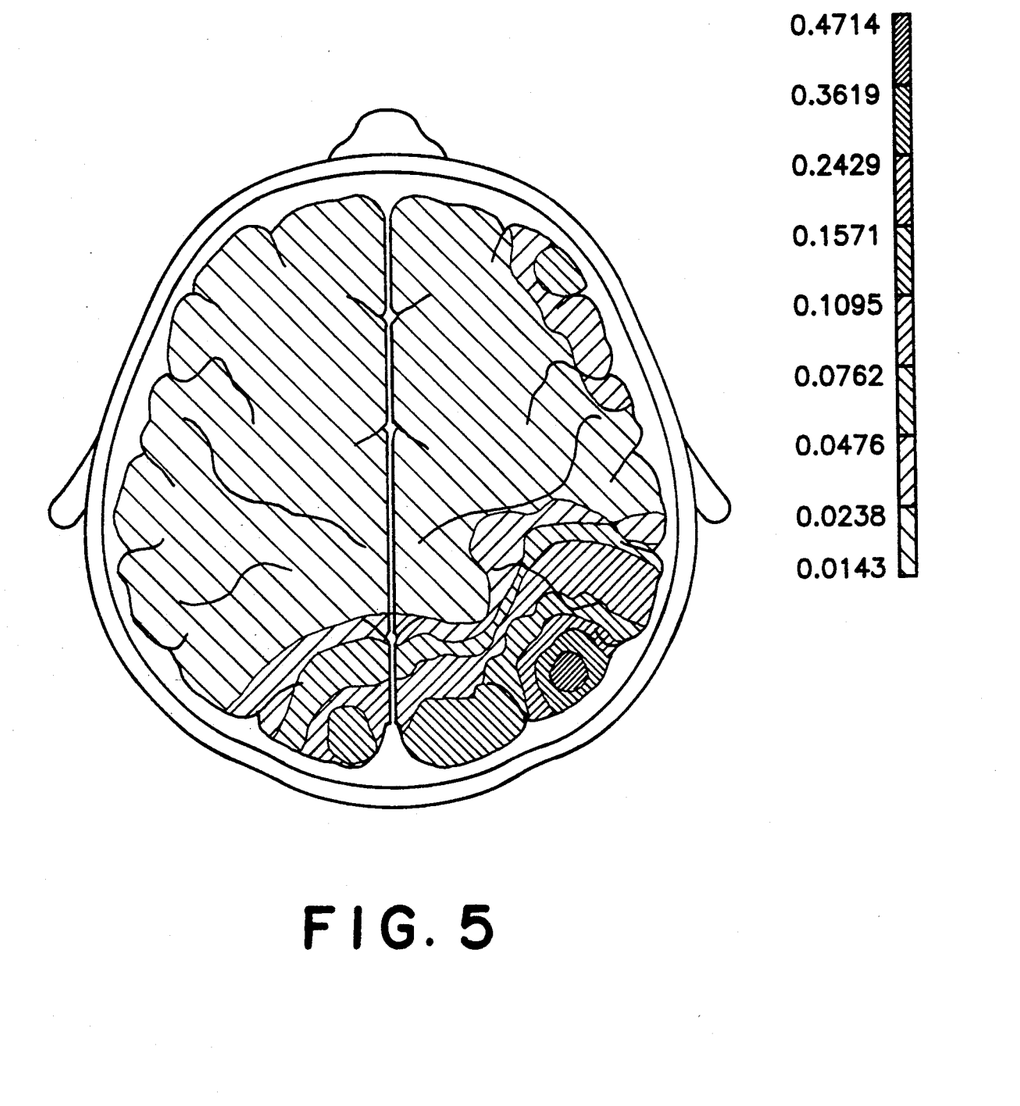
FIG. 5 shows a Typified Maximal Abnormality Directional Map with the maximum probability scale for a patient with a deep frontotemporal tumor.
Figure 6:
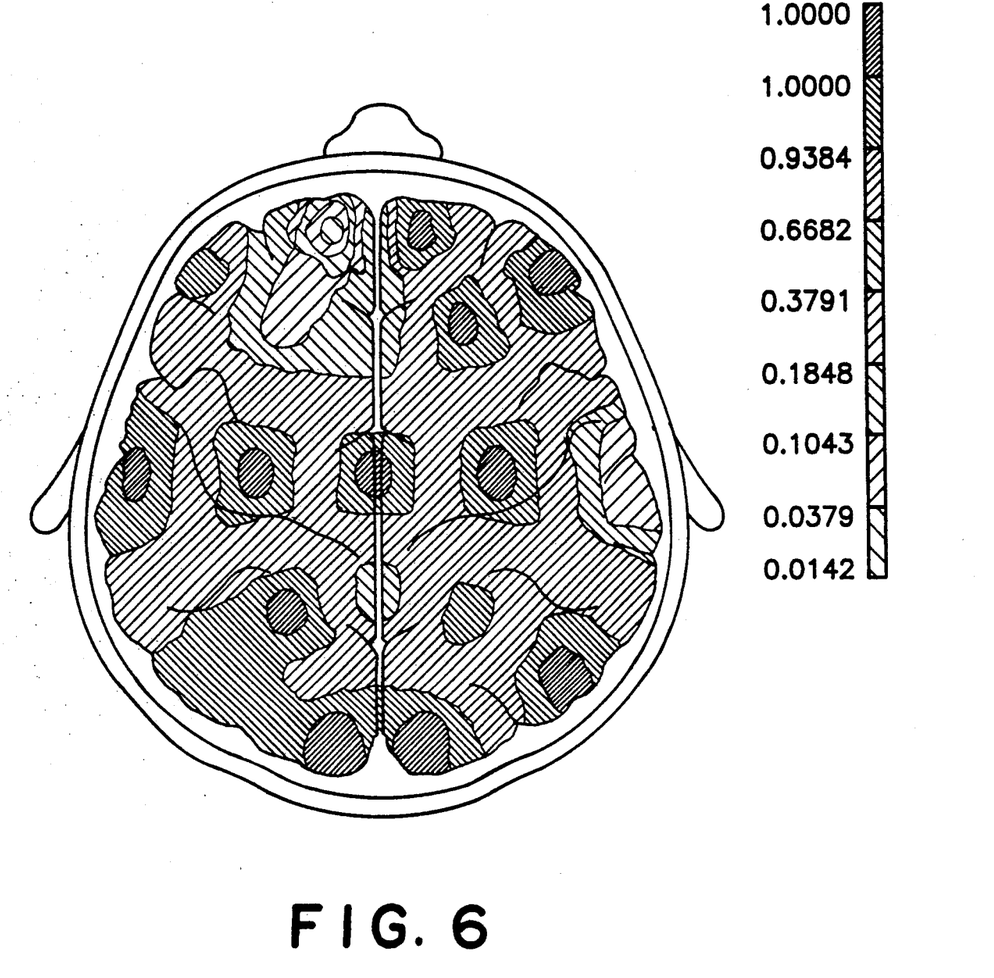
FIG. 6 shows a Topographic Brain Map of conditional Z values with the maximum probability scale for the same patient as in FIG. 5.

The use of Multivariate maps is further illustrated in FIG. 5 and 6. FIG. 5 shows a Maximal Abnormality Directional Map with the maximum probability scale for a patient with a deep left frontotemporal tumor. FIG. 6 shows a Topographic Brain Map of conditional Z values with the maximum probability scale for the same patient as in FIG. 5.

We claim:

1. A method for the evaluation and visual display of abnormal electromagnetic physiological data of the brain and the heart, said method including the steps of:
    a) positioning a set of electrodes and magnetic sensors and detecting electromagnetic physiological activity of a patient in the form of electromagnetic data signals selected from the group consisting of electroencephalogram (EEG), magnetoencephalogram (MEG), brain evoked response (ER), electrocardiogram (EKG), and magnetocardiogram (MKG) data signals;
    b) amplifying the electromagnetic signals detected at each electrode and magnetic sensor;
    c) obtaining on-line digital spatio-temporal signals, consisting of said EEG, MEG, ER, EKG, and MKG signals, by connecting analog-digital converters to each amplifier, and digitizing all data as it is gathered;
    d) obtaining sets of said spatio-temporal signals for the patient, and computing coefficients of expansion of the signals in a spatio-temporal functional basis defined by a tensorial product of selected functional bases for spatial and temporal domains,;
    e) computing estimates of parameters determined by statistical parametric models for probabilistic moments of said coefficients for a patient;
    f) automatically constructing summarized topographic maps by a process of diagnostically useful summarization of information contained in said sets of signals or probabilistic moments corresponding to different instants or frequencies, and automatically constructing summarized curves by a process of summarization of the information contained in said sets of signals or probabilistic moments corresponding to different electrodes and magnetic sensors;
    g) computing multivariate topographic maps and curves based on a comparison of said summarized topographic maps and curves with their means, standard deviations and correlations in stored normative data bases from normal subjects;
    h) visually displaying said multivariate topographic maps and curves in a diagnostically useful color-coded probability scale.

2. A method as claimed in claim 1 wherein the functional basis for the temporal domain is a trigonometric basis and said parameters are variances of Fourier coefficients for each electrode and frequency, said method further comprising the steps of estimating said variances by a sample spectrum or periodogram; computing normative mean values, standard deviations and correlations of the periodogram by a non-linear and heteroscedastic regression analysis of a log-periodogram as a function of frequency and age for each electrode, using a stored normative data base of normal subjects; and performing said regression analysis based upon mean and variance regression functions constructed by the tensorial product of a polynomial basis for the age and a spline basis for the frequency domain.

3. A method as claimed in claim 1 further comprising the step of constructing said functional basis by computing a tensorial product of a trigonometric basis a time domain and a reproducing kernel basis determined by positions of the set of electrodes and a norm of functional smoothness for a spatial domain; and wherein said parameters are the parameters of a multivariate autoregressive time series model for a vector of coefficients of the expansion in said spatial functional basis.

4. A method as claimed in claim 1 further comprising the step of computing said parametric model for said probabilistic moments based upon a multiple dipole source model.

5. A method as claimed in claim 1 further comprising the step of computing the spatio-temporal basis as a wavelet basis in order to account for nonstationarities and for multiresolution representation of said sets of signals.

6. A method as claimed in claim 1 further comprising the step of obtaining the multivariate topographic maps and curves of a given patient by computing a residual of each value of the patient's summarized map or curve with respect to its expected value, given remaining values of the patient, in accordance with a probability distribution of a normative population stored in a computer memory.

7. A method as claimed in claim 1 further comprising the step of obtaining the multivariate topographic maps and curves of a given patient by computing a vector which points in a direction of maximal statistical deviation of the patient's summarized map or curve from the map or curve representative of a normative population.

8. A method as claimed in claim 1 wherein the step of visually displaying said multivariate topographic maps and curves is carried out using the probability values defined by distribution functions of a maximum and minimum of said maps and curves stored in a normative database, and the representation of these probability values by a color-coded scale.

9. A system for the evaluation and visual display of abnormal electromagnetic physiological data of the brain and the heart that comprises:
   a) a set of electrodes and/or magnetic sensors adapted to be positioned relative to the scalp or torso of a patient in order to detect electromagnetic physiological activity by detecting electromagnetic signals selected from the group consisting of the following signals: electroencephalogram (EEG), magnetoencephalogram (MEG), brain evoked response (ER), electrocardiogram (EKG), and magnetocardiogram (MKG);
   b) means for amplifying said electromagnetic signals to obtain amplified electromagnetic signals;
   c) means for analog-to-digital conversion of the amplified electromagnetic signals to obtain digital spatio-temporal signals, representative of the aforementioned EEG, MEG, EKG, and MKG;
   d) means for storing sets of said spatio-temporal signals for the patient, and for computing coefficients of expansion in a spatio-temporal functional basis defined by a tensorial product of selected functional bases for spatial and temporal domains;
   e) means for computing estimates of parameters determined by statistical parametric models for probabilistic moments of said coefficients for a patient;
   f) means for automatic construction of summarized topographic maps by a process of diagnostically useful summarization of information contained in said sets of signals or probabilistic moments corresponding to different instants or frequencies, and automatic construction of summarized curves by a process of summarization of the information contained in a said sets of signals or probabilistic moments corresponding to different electrodes and magnetic sensors;
   g) means for computing multivariate topographic maps and curves for a given patient based on a comparison of said summarized topographic maps and curves with their means, standard deviations and correlations in stored normative data bases from normal subjects;
   h) means for visually displaying said multivariate topographic maps and curves in a diagnostically useful color-coded probability scale.

* * * * *